United States Patent
Lee et al.

(10) Patent No.: US 11,162,941 B2
(45) Date of Patent: Nov. 2, 2021

(54) IMMUNOASSAY CARTRIDGE

(71) Applicant: OPTOLANE Technologies Inc., Seongnam-shi (KR)

(72) Inventors: Do Young Lee, Seoul (KR); Kyung Hak Choi, Yongin-shi (KR)

(73) Assignee: OPTOLANE TECHNOLOGIES INC., Seongnam-shi (KR)

( * ) Notice: Subject to any disclaimer, the term of this patent is extended or adjusted under 35 U.S.C. 154(b) by 173 days.

(21) Appl. No.: 15/881,986

(22) Filed: Jan. 29, 2018

(65) Prior Publication Data
US 2018/0238872 A1 Aug. 23, 2018

(30) Foreign Application Priority Data

Feb. 17, 2017 (KR) .................. 10-2017-0021642

(51) Int. Cl.
| | |
|---|---|
| *G01N 33/543* | (2006.01) |
| *B01L 3/00* | (2006.01) |
| *G01N 21/64* | (2006.01) |
| *G02B 5/22* | (2006.01) |
| *G01N 21/76* | (2006.01) |
| *G01N 21/03* | (2006.01) |

(52) U.S. Cl.
CPC .. *G01N 33/54393* (2013.01); *B01L 3/502715* (2013.01); *G01N 21/645* (2013.01);
(Continued)

(58) Field of Classification Search
CPC .......... G01N 33/54393; G01N 21/645; G01N 33/533; G01N 21/6454; G01N 21/76;
(Continued)

(56) References Cited

U.S. PATENT DOCUMENTS

| | | | |
|---|---|---|---|
| 6,438,279 B1* | 8/2002 | Craighead .............. | G02B 6/136 356/246 |
| 2006/0233670 A1* | 10/2006 | Lehto ................... | B01L 3/0293 422/400 |

(Continued)

FOREIGN PATENT DOCUMENTS

| | | |
|---|---|---|
| CN | 101008686 | 8/2007 |
| CN | 101802709 | 8/2010 |

(Continued)

OTHER PUBLICATIONS

Extended European Search Report for European Application No. 18155713, dated Jul. 26, 2018.
(Continued)

*Primary Examiner* — Dennis White
(74) *Attorney, Agent, or Firm* — Kile Park Reed & Houtteman PLLC

(57) ABSTRACT

An immunoassay cartridge is disclosed that can enhance the reliability of an antigen-antibody reaction while increasing a speed of an antigen-antibody reaction. An immunoassay cartridge includes a reaction chamber and a fluorescence sensor assembly. A plurality of antibodies or antigens is attached to an inner surface including a bottom surface of the reaction chamber closest to the sensor. The fluorescence sensor assembly is disposed on a bottom surface of the reaction chamber. Since the bottom surface of the reaction chamber and the upper surface of the fluorescence sensor assembly are arranged to coincide with each other, even if fluid is repeatedly moved in a first direction after the fluid moves in a second direction in the reaction chamber and then moved in the first direction, there is no obstacle in the movement of the fluid. Thus, it is possible to increase the probability of antigen-antibody reaction in the reaction chamber.

12 Claims, 5 Drawing Sheets

(52) U.S. Cl.
CPC ......... *G01N 21/6454* (2013.01); *G01N 21/76* (2013.01); *G01N 33/54366* (2013.01); *G02B 5/223* (2013.01); *B01L 3/502738* (2013.01); *B01L 2200/027* (2013.01); *B01L 2300/069* (2013.01); *B01L 2300/0627* (2013.01); *B01L 2300/0654* (2013.01); *B01L 2300/0663* (2013.01); *B01L 2300/0681* (2013.01); *B01L 2300/0816* (2013.01); *B01L 2400/0481* (2013.01); *B01L 2400/06* (2013.01); *G01N 2021/0325* (2013.01); *G01N 2021/6471* (2013.01); *G01N 2021/6482* (2013.01)

(58) Field of Classification Search
CPC ..... G01N 33/54366; G01N 2021/6471; G01N 2021/6482; G01N 2021/0325; G02B 5/223; B01L 2300/0654; B01L 2400/06; B01L 2300/0681; B01L 2300/0627; B01L 3/502715; B01L 3/502738; B01L 2400/0481; B01L 2300/069; B01L 2300/0663; B01L 2300/0816; B01L 2200/027
See application file for complete search history.

(56) References Cited

U.S. PATENT DOCUMENTS

| | | | |
|---|---|---|---|
| 2010/0093553 A1* | 4/2010 | Park | G01N 33/54353 506/9 |
| 2011/0260950 A1* | 10/2011 | Jung | G09G 3/3426 345/5 |
| 2012/0196775 A1 | 8/2012 | Taguchi | |
| 2014/0001041 A1* | 1/2014 | Rahman | C12M 41/36 204/403.01 |
| 2014/0170678 A1* | 6/2014 | Kasdan | B01L 3/502 435/7.24 |
| 2015/0290639 A1* | 10/2015 | Evtodienko | G01N 33/558 435/7.94 |
| 2015/0291929 A1 | 10/2015 | Murphy et al. | |
| 2016/0047747 A1 | 2/2016 | Lafferty et al. | |
| 2016/0108161 A1 | 4/2016 | Kaneko et al. | |
| 2016/0341656 A1* | 11/2016 | Liu | G01N 21/6454 |
| 2017/0016827 A1* | 1/2017 | Gervais | G01N 21/6428 |

FOREIGN PATENT DOCUMENTS

| | | |
|---|---|---|
| CN | 102621112 | 8/2012 |
| CN | 102859572 | 1/2013 |
| CN | 103645308 | 3/2014 |
| CN | 105339438 | 2/2016 |
| CN | 106233124 | 12/2016 |
| EP | 0 733 714 A2 | 9/1996 |
| EP | 0 733 714 A3 | 4/1997 |
| EP | 1 256 795 A2 | 11/2002 |
| EP | 1 256 795 A3 | 3/2006 |

OTHER PUBLICATIONS

Partial European Search Report for European Application No. EP 18 15 5713, dated May 11, 2018.

* cited by examiner

IMMUNOASSAY CARTRIDGE

CROSS-REFERENCE TO RELATED APPLICATIONS

This application claims priority under 35 U.S.C. § 119 to Korean Patent Application No. 10-2017-0021642, filed on Feb. 17, 2017 in the Korean Intellectual Property Office (KIPO), the contents of which are herein incorporated by reference in their entirety.

BACKGROUND OF THE INVENTION

1. Technical Field

Exemplary embodiments of the present invention relate to an immunoassay cartridge. More particularly, exemplary embodiments of the present invention relate to an immunoassay cartridge capable of enhancing the reliability of an antigen-antibody reaction while increasing a speed of an antigen-antibody reaction.

2. Description of the Related Art

A device for inspection or investigation of the existence of one or a plurality of substances in the liquid sample, for example, or require a blood sample is referred to as diagnostic kits. Specifically, the diagnostic business of the modern on-site inspection (Point-Of-Care Testing: POCT) are integrated into one. POCT refers to equipment that the public can not be made outside expertise to a centralized laboratory tests. Currently there is a trend in this field from the hospital and individual diagnostic area is expanded.

For example, in a hospital, the patient may need to examine whether getting a large amount of antibiotics administered to fight the infection, then antibiotics right amount of presence in the blood collecting a small amount of blood or recognition in the case of an infant that can not be damaged or excessive intake of patients with communication, it can be such that the application of the rapid survey of the types of drugs consumed in the human body in order to ensure the appropriate treatment administered. Rapid diagnostic testing as typified in particular, immune chromatographic analysis examines the trace amounts of analytes in is used to determine the diseases in the health care field or changing areas diverse as food and bioprocess applications, environmental qualitatively and quantitatively It has been developed in a simple way. In the health care field, it has been expanded scope of application of pregnancy, ovulation, infectious diseases, drugs of abuse, such as acute myocardial infarction and cancer.

SUMMARY

Exemplary embodiments of the present invention provide an immunoassay cartridge capable of enhancing the reliability of an antigen-antibody reaction while increasing the speed of an antigen-antibody reaction.

According to one aspect of the present invention, an immunoassay cartridge includes a reaction chamber and a fluorescence sensor assembly. A plurality of antibodies or antigens is attached to an inner surface including a bottom surface of the reaction chamber closest to the sensor. The fluorescence sensor assembly is disposed on a bottom surface of the reaction chamber.

In an exemplary embodiment of the present invention, the immunoassay cartridge may further include an input-micro flow path formed between an inlet and the reaction chamber; one or more blisters; and a sub-micro flow path formed between the blister and the input-micro flow path.

In an exemplary embodiment of the present invention, the immunoassay cartridge may further include a valve disposed in the sub-micro flow path to control a flow of a fluid.

In an exemplary embodiment of the present invention, the immunoassay cartridge may further include an output-micro flow path connected to the reaction chamber; an output chamber connected to the reaction chamber through the output-micro flow path; and an air button connected to the output chamber, the air button supplying air to the output-micro flow path via the output chamber in response to an operation of an operator.

In an exemplary embodiment of the present invention, the fluorescence sensor assembly may include an emission filter disposed below the reaction chamber, the emission filter having an optical characteristic capable of filtering regardless of an incident angle of the excitation light and transmitting a radiation light having a wavelength larger than that of the excitation light.

In an exemplary embodiment of the present invention, the fluorescence sensor assembly may further include a single sensor disposed below the emission filter, the single sensor constituting a fluorescent sensor array or an array measuring the luminance of the emission light that has passed through the emission filter.

In an exemplary embodiment of the present invention, the emission filter may include a base medium arranged in a flat shape and including a material which is transparent and which does not generate fluorescence or phosphorescence by excitation light; a photoresist disposed in the base medium and fixed in a solid state by at least one method selected from the group consisting of thermosetting, photocuring and drying; and a pigment disposed in the base medium and absorbing light of a predetermined wavelength.

In an exemplary embodiment of the present invention, the single sensor comprises: a base substrate having a flat plate shape and integrally formed with the emission filter; and a plurality of fluorescence sensors embedded in an upper portion of the base substrate, the fluorescence sensors arranged in an array so that the upper surface of the base substrate is planar.

In an exemplary embodiment of the present invention, the immunoassay cartridge may further include a printed circuit board electrically connected to the fluorescent sensor assembly through solder balls.

In an exemplary embodiment of the present invention, the fluorescence sensor assembly may have a flat shape, and a bottom surface of the reaction chamber and an upper surface of the fluorescence sensor assembly may be aligned with each other.

In an exemplary embodiment of the present invention, the antibody or antigen may be mixed into a two-dimensional or three-dimensional structure.

In an exemplary embodiment of the present invention, the location-based material may be attached to an inner surface including a bottom surface of the reaction chamber in the form of a dot with an array of rows and columns.

In an exemplary embodiment of the present invention, the location-based material may include at least one of dendron and hydrogel pad.

According to some exemplary embodiments of the present invention, since the bottom surface of the reaction chamber and the upper surface of the fluorescence sensor assembly are arranged to coincide with each other, even if fluid is repeatedly moved in a first direction after the fluid moves in a second direction in the reaction chamber and then moved in the first direction, there is no obstacle in the movement of the fluid. Thus, it is possible to increase the probability of antigen-antibody reaction in the reaction chamber. Further, blood is supplied to the reaction chamber by pressurization of the inlet, and the direction of movement of the blood in the reaction chamber is changed by pressing the air button, thereby speeding up the blood movement speed. Thus, it is possible to increase the likelihood of exposure to an antigen-antibody reaction between an antibody or antigen mixed with a location-based material (e.g., a hydrogel pad) and an antigen or antibody contained in the blood. In addition, the fluid in the blister (e.g., a cleaning liquid) is supplied to the reaction chamber through a method of pressurizing various blisters, and the direction of movement of the fluid in the reaction chamber is changed through a method of pressing the air button, thereby increasing the moving speed of the fluid. Therefore, the cleaning probability of contaminated portions other than the hydrogel pad may be increased. Thus, the reliability of the antigen-antibody reaction may be improved while increasing the speed of the antigen-antibody reaction.

BRIEF DESCRIPTION OF THE DRAWINGS

The above and other features and aspects of the present invention will become more apparent by describing in detailed exemplary embodiments thereof with reference to the accompanying drawings, in which.

DETAILED DESCRIPTION OF THE INVENTION

Figure 1:
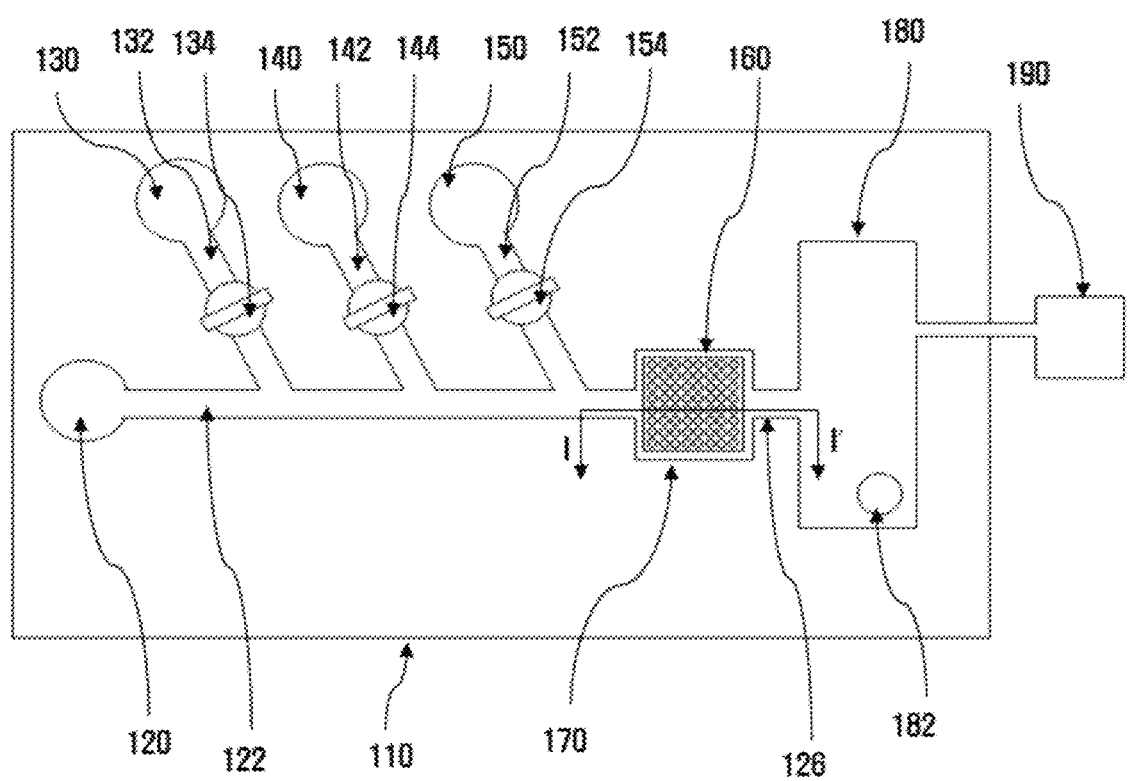
FIG. 1 is a schematic view schematically explaining an immunoassay cartridge according to an exemplary embodiment of the present invention.

The present invention is described more fully hereinafter with reference to the accompanying drawings, in which exemplary embodiments of the present invention are shown. The present invention may, however, be embodied in many different forms and should not be construed as limited to the exemplary embodiments set forth herein. Rather, these exemplary embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular exemplary embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Exemplary embodiments of the invention are described herein with reference to cross-sectional illustrations that are schematic illustrations of idealized exemplary embodiments (and intermediate structures) of the present invention. As such, variations from the shapes of the illustrations as a result, for example, of manufacturing techniques and/or tolerances, are to be expected. Thus, exemplary embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, the present invention will be explained in detail with reference to the accompanying drawings.

FIG. 1 is a schematic view schematically explaining an immunoassay cartridge according to an exemplary embodiment of the present invention.

Referring to FIG. 1, an immunoassay cartridge according to an exemplary embodiment of the present invention includes a base member 110, an inlet 120, an input-micro flow path 122, a first blister 130, a first sub-micro flow path 132, a first valve 134, a second blister 140, a second sub-micro flow path 142, a second valve 144, a third blister 150, a third sub-micro flow path 152, a third valve 154, a reaction chamber 160, a fluorescence sensor assembly 170, an output chamber 180 and an air button 190.

The inlet 120, the input-micro flow path 122, the first blister 130, the first sub-micro flow path 132, the first valve 134, the second blister 140, the second sub-micro flow path 142, the second valve 144, the third blister 150, the third sub-micro path 152, the third valve 154, the reaction chamber 160, the fluorescence sensor assembly 170 and the output chamber 180 may be disposed on the base member 110. The base member 110 may include a pressure sensitive adhesive tape.

The inlet 120 receives a sample such as blood. The inlet 120 supplies the blood to the reaction chamber 160 via the input-micro flow path 122 by an operation of an operator, for example, the pressing of a finger or a mechanical pressing device.

The input-micro flow path 122 is formed between the inlet 120 and the reaction chamber 160.

Figure 2:
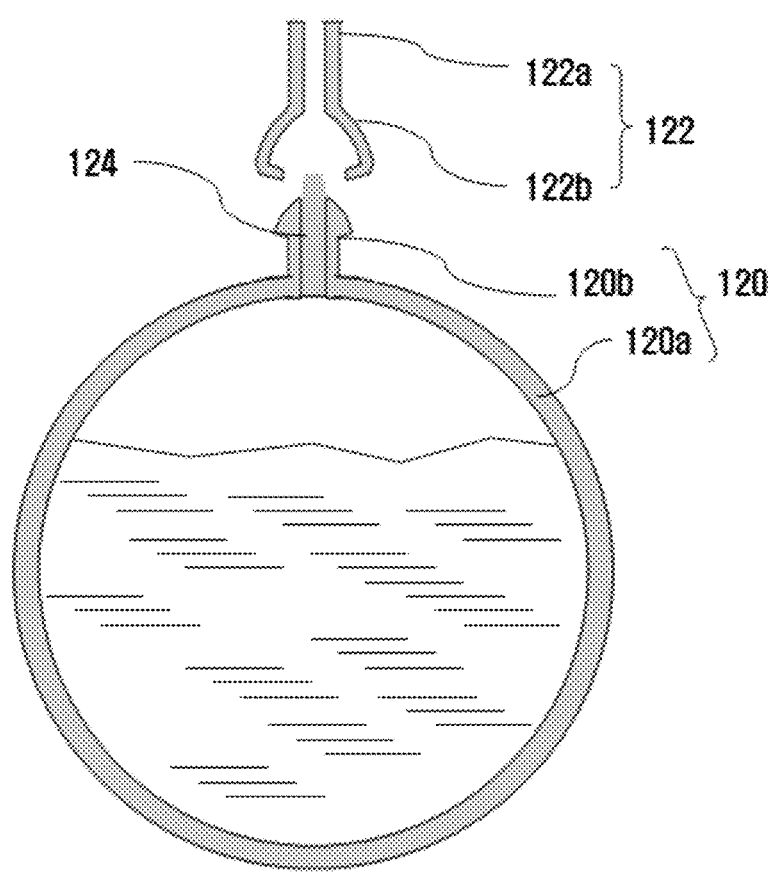
FIG. 2 is a conceptual diagram schematically illustrating a connection structure of an inlet and an input-micro flow path shown in FIG. 1.

FIG. 2 is a conceptual diagram schematically illustrating a connection structure of an inlet 120 and an input-micro flow path 122 shown in FIG. 1.

Referring to FIG. 2, the inlet 120 includes a body portion 120a having a rectangular shape, a circular shape or various shapes capable of accommodating a liquid such as a syringe, and a first coupling portion 120b protruded from the body portion 120a. A space for accommodating a sample such as blood is formed in the body portion 120a. The body portion 120a supplies the sample such as blood to the input-micro flow path 122 through the first coupling portion 120b as a finger of an operator or the mechanical pressing device is pressed. In FIG. 2, it is described that the body portion 120a has a circular shape; however, the body portion 120a may have a polygonal shape such as a triangle shape, a square shape, or the like.

The input-micro flow path 122 includes a flow path portion 122a for providing a flow path of a fluid and a second coupling portion 122b formed at an end portion of the flow path portion 122a. The second coupling portion 122b is coupled to the first coupling portion 120b of the inlet 120. In the present embodiment, the first coupling portion 120b has a bolt-like shape and the second coupling portion 122b has a nut-like shape, so that the first coupling portion 120b may be coupled to the second coupling portion 122b.

In order to diagnose a specific blood using the immunoassay cartridge, an immunoassay cartridge according to an exemplary embodiment of the present invention performs an immunodiagnostic operation by coupling the inlet 120 containing the specific blood to the input-micro flow path 122, and the inlet 120 in which the immunodiagnostic operation is completed may be separated from the immunoassay cartridge in accordance with an operation of the operator.

In this way, the inlet 120 may be separated from the immunoassay cartridge, so that blood may be directly sucked through a hole of the end of the inlet 120. For example, it exposes blood by scarring the tip of a finger. Then, the hole of the inlet 120 may be brought into contact with the blood drop and sucked while the inlet 120 is being pressed.

A filter 124 may be further disposed between the inlet 120 and the input-micro flow path 122 to pass only the blood plasma.

Although the connection structure between the inlet 120 and the input-micro flow path 122 has been described above, this technique may be similarly applied to the connection structure between the first blister 130 and the first sub-micro flow path 132, the connection structure between the second blister 140 and the second sub-micro flow path 142 and the connection structure between the third blister 150 and the third sub-micro flow path 152.

Referring again to FIG. 1, the first blister 130 is connected to the input-micro flow path 122 via the first sub-micro flow path 132. Here, a first valve 134 for blocking the flow of the fluid may be disposed in the first sub-micro flow path 132. In the present exemplary embodiment, a first cleaning liquid may be provided to the first blister 130. The first cleaning liquid may be supplied to the reaction chamber 160 through the first sub-micro flow path 132 as the first blister 130 is pressed by a finger of an operator or a mechanical pressing device.

The second blister 140 is connected to the input-micro flow path 122 via the second sub-micro flow path 142. Here, the second valve 144 for blocking the flow of the fluid may be disposed on the second sub-micro flow path 142. In the present exemplary embodiment, the second blister 140 may contain a reactant (fluorescent material). The reactant may be provided to the reaction chamber 160 through the second sub-micro flow path 142 as the second blister 140 is pressed by a finger of an operator or the mechanical pressing device.

The third blister 150 is connected to the input-micro flow path 122 via the third sub-micro flow path 152. Here, a third valve 154 for blocking the flow of the fluid may be disposed on the third sub-micro flow path 152. In the present exemplary embodiment, the third blister 150 may contain a second cleaning liquid. The second cleaning liquid may be supplied to the reaction chamber 160 through the third sub-micro flow path 152 as the third blister 150 is pressed by a finger of an operator or the mechanical pressing device. In the present exemplary embodiment, the first cleaning liquid or the second cleaning liquid may include breeze (BRIJ), Triton (TRITON), tween (tWEEN), Te sheet (THESIT), Lu beurol (LUBROL), the Napoletana (GENAPOL), Nick (PLURONIC) Pluronic includes, Tetronic (TETRONIC), and span (sPAN) under the trade name known non-ionic cleaning liquid or surfactant in the class.

In the present exemplary embodiment, although it has been described that three blisters 130, 140 and 150, three sub-micro flow paths 132, 142 and 152, and three valves 134, 144 and 154 are disposed as an example, it is not limited thereto. Alternatively, two blisters, two sub-micro flow paths and two valves may be disposed thereon, and four or more blisters, four or more sub-micro flow paths, and four or more valves may be disposed thereon.

The reaction chamber 160 is connected to the inlet 102 through the input-micro flow path 122 and is connected to the output chamber 180 through the output-micro flow path 126. Moreover, since the first sub-micro flow path 132 is connected to the input-micro flow path 122, the reaction chamber 160 is connected to the first blister 130 through the first sub-micro flow path 132. Moreover, since the second sub-micro flow path 142 is connected to the input-micro flow path 122, the reaction chamber 160 is connected to the second blister 140 through the second sub-micro flow path 142. Moreover, since the third sub-micro flow path 152 is connected to the input-micro flow path 122, the reaction chamber 160 is connected to the third blister 150 through the third sub-micro flow path 152.

Figure 3:
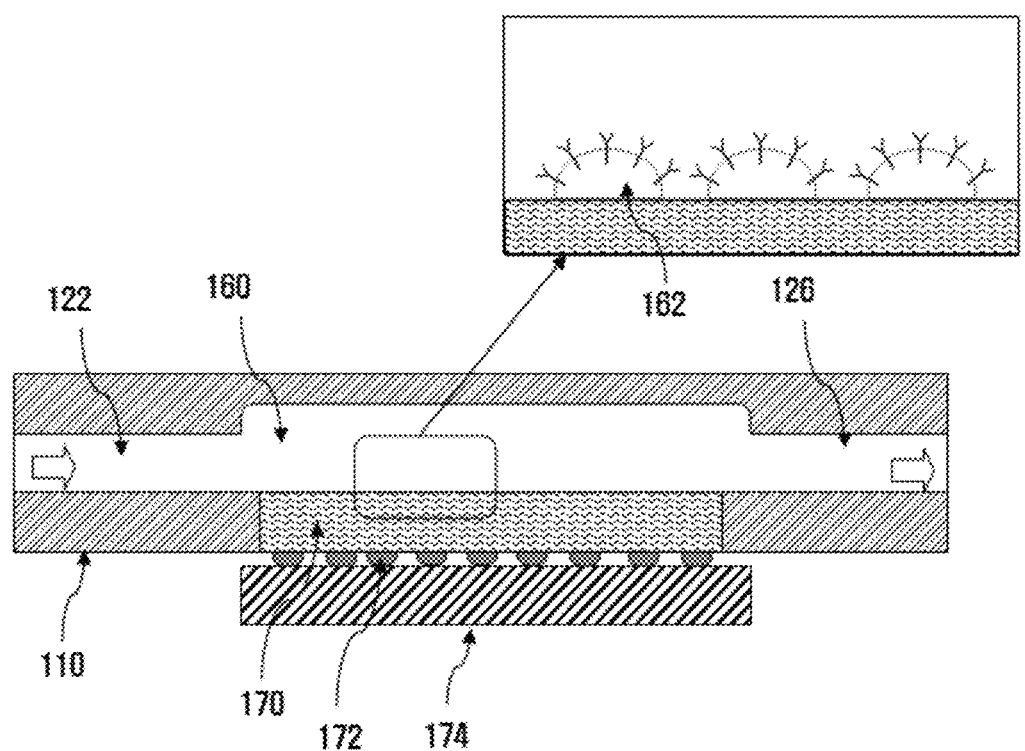
FIG. 3 is a cross-sectional view taken along the line I-I' of a reaction chamber shown in FIG. 1'.

FIG. 3 is a cross-sectional view taken along the line I-I' of a reaction chamber 160 shown in FIG. 1.

Referring to FIG. 3, a position-based material (Dendron, hydrogel pad, or the like) that binds to an antibody or an antigen is attached in an inner surface including the bottom surface of the reaction chamber 160 in the form of dots in an array of rows. When the hydrogel is mixed with water, the hydrogel of the hydrogel pad 162 is not melted or dissolved but is cross-linked into high polymer chains or polymer chins, thereby maintaining 3-dimensional structure. The hydrogel is hydrophilic material and includes polymer chains forming a plurality of cross-links. For example, the hydrogel may include various kinds of hydrogels such as polyethylene diacrylate (PEGDA) hydrogel, PMA hydrogel, polydimethylamino acrylamide (PDGPA) hydrogel, polyethyloxazoline, silicon hydrogel, etc. In the embodiment of the present invention, the hydrogel pad 162 may include PEGDA hydrogel.

Each of the hydrogel pads 162 is mixed with a plurality of different antibodies or antigens. In the present embodiment, the term "antibody" may include a recombinant protein construct including an intact antibody molecule, an antibody fragment and an antigen binding domain of the antibody. Moreover, the term "antibody" refers to a specific component for biological material analysis, which is a component for quantitative or qualitative analysis of a specific biological material, for example, protein, DNA, RNA, etc., as a primer, a probe, an antibody, a polymerase, and the like. In particular, the term "antibody" may mean a necessary component for performing a real-time PCR, a constant temperature enzyme reaction, or an LCR (Ligase Chain Reaction).

In the present exemplary embodiment, the term "antigen" is well understood in the art and includes substances which are immunogenic, i.e., immunogens, as well as substances which induce immunological unresponsiveness, or anergy, i.e., anergens. Where the antigen is a polypeptide, it may be a transmembrane molecule (e.g. receptor) or ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)—IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

Moreover, in the case of the conventional array method, an immunodiagnosis speed is slow because dielectric substances are disposed only on a surface. However, the hydrogel pads 162 disclosed in the present embodiment have a high immunodiagnosis speed because the antigen antibody reaction occurs not only on the surface of the hydrogel pads 162 but also inside of the hydrogel pads 162 due to a three-dimensional structure of the polymer chains. Therefore, an array is formed by the hydrogel pads 162, so that real-time immunodiagnosis is possible by position. Further, since the fluorescence exits only from the hydrogel pad 162, the amount of light increases. Therefore, the intensity of the detected signal increases, and more sensitive experiments are possible.

That is, since the hydrogel has a porous property, the blood or the reactant can freely move. Therefore, the probability of the antigen-antibody reaction with the antibody may be increased. In the present exemplary embodiment, the various antibodies or antigens mixed in the hydrogel of the hydrogel pad 162 may be attached in a matrix form to define an antibody or an antigen microarray.

The reaction chamber 160 is disposed to measure an analytical signal by binding or reacting with an analyte present in the sample. When a sample is introduced into the reaction chamber 160, an enzyme reaction, an immunoreaction, a chemical reaction, a hybridization reaction of DNA or RNA, a coagulation aggregation and agglutination reactions are occurred in the analyte of the sample to generate a detection signal by the analyte. The analytical signals may be analyzed by an optical method such as coloration, luminescence, fluorescence, refractive index change, FRET(fluorescence resonance energy transfer), etc., an electrochemical method through oxidation/reduction, a quartz crystal microbalance method or a microcantilever method and the like. In order to generate a detection signal by the analyte, the reaction chamber 160 may further include an enzyme, an antigen, an antibody, a DNA, an RNA, an apatmer, a ligand, a receptor, a binding probe, an enzyme substrate, and the like. Since the volume of the sample introduced into the reaction chamber 160 must be accurately determined according to need, various types of electrodes may be introduced into the reaction chamber 160 to electrochemically measure a conductivity change between electrodes or a change of resistance by introducing of the sample, so that the volume of the sample introduced into the reaction chamber 160 may be quantified. Alternatively, when the reaction chamber 160 is transparent, the volume of the sample introduced into the reaction chamber 160 through the spectroscopic method may be quantified.

The fluorescence sensor assembly 170 has a flat shape, and the bottom surface of the reaction chamber 160 and the upper surface of the fluorescence sensor assembly 170 are arranged to coincide with each other. That is, the fluorescence sensor assembly 170 is disposed, so that the imaginary lines extending in the horizontal direction on the bottom surface of the reaction chamber 160 and the imaginary lines extending in the horizontal direction on the upper surface of the fluorescence sensor assembly 170 coincide with each other.

A back surface of the fluorescent sensor assembly 170 may be electrically connected to the printed circuit board 175 through solder balls 173. The solder balls 173 may be disposed on the printed circuit board 175, and the fluorescent sensor assembly 170 may be disposed on the solder balls 173.

The fluorescence sensor assembly 170 is disposed on a bottom surface of the reaction chamber 160. The fluorescence sensor assembly 170 photographs an image in plan view for image analysis in which a chemiluminescent signal generated by an immune reaction in each antibody spot is measured for each pixel and the microscopic signal is interpreted as a meaningful value.

Typically, Fluorescence Lifetime Imaging (FLIM) technology is a technique that, when the fluorescence generated in the fluorescent substance exponentially decreases, visualizes changing of the time constant measured by using the fact that the time constant of the fluorescent substance substance, which is a characteristic of the fluorescent substance substance, changes depending on the surrounding environment. Here, a fine amount of fluorescence may be detected without using an emission filter by applying a measuring method of the time constant.

Figure 4:
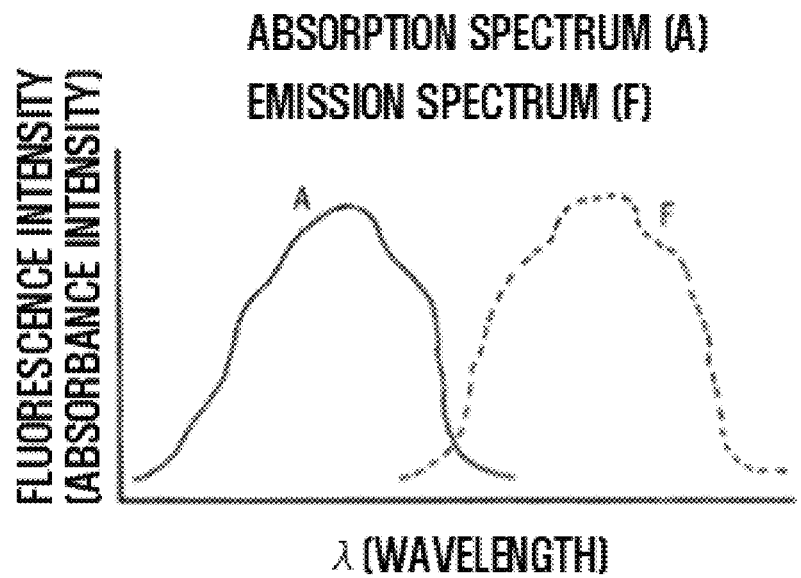
FIG. 4 is a graph explaining a spectrum of a fluorescent material.

Generally, as shown in FIG. 4, a fluorescent material emits fluorescence light having a long wavelength band when light having a specific wavelength band according to its intrinsic property is received. At this time, as shown in FIG. 3, the emitted fluorescent light has an exponentially decreasing property that an initial value is n(0) and a time constant is $\tau$.

The time constant of a curve that exponentially decreases with respect to n(T1) and n(T2), which are the amounts of fluorescence light measured at different times T1 and T2 after fluorescence light is emitted, may be obtained as follows.

The emission light emitted as a result of a bio-reaction is fluorescence light having a long wavelength relative to a wavelength of an excitation light. If it should detect the fluorescence light, it is need an emission filter that removes the excitation light and passes the fluorescence light. Alternatively, if the excitation light does not exist when detecting fluorescence, the emission filter may be omitted.

Figure 5:
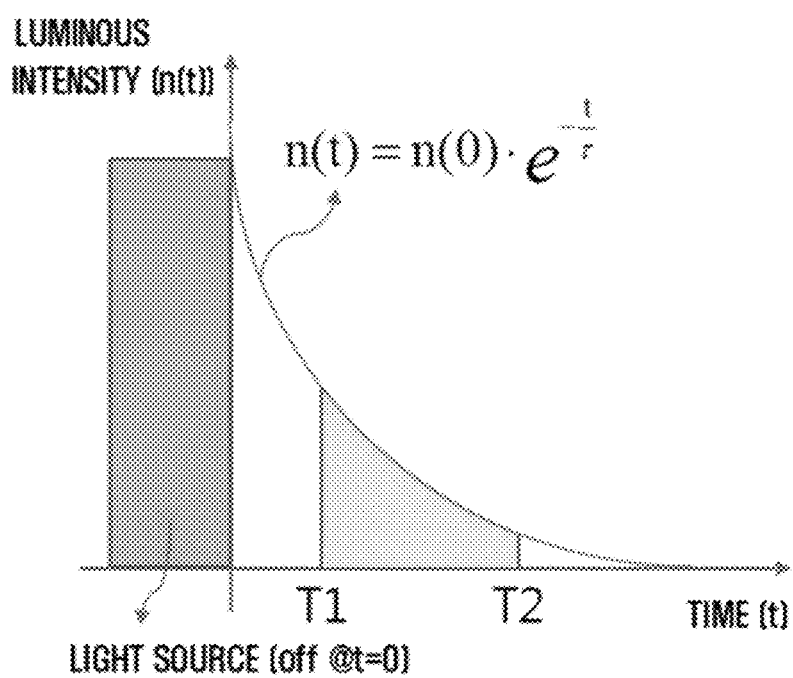
FIG. 5 is a graph explaining fluorescence emitted according to excitation light.

In FIG. 5, when the light source corresponding to the excitation light is turned off at time t=0, the fluorescence in response to the excitation light exponentially decreases from the value at time t=0 with the time constant $\tau$.

Since the excitation light source is already turned off during the exponential decay of the fluorescence, the fluorescence to be detected only exists. When the sensor is exposed during time T2−T1 at time T1, the amount of fluorescence in this section can be obtained.

In this case, only a portion of the entire fluorescence is detected, so that the amount thereof may be small. Therefore, when the fluorescence value sensed at each exposure is added by repeating the process of exposing the excitation light to a single sensor constituting a fluorescence sensor array or an array, it may obtain a sufficient amount of fluorescence amount. In the above-described manner, an emission filter for removing excitation light is unnecessary.

Figure 6:
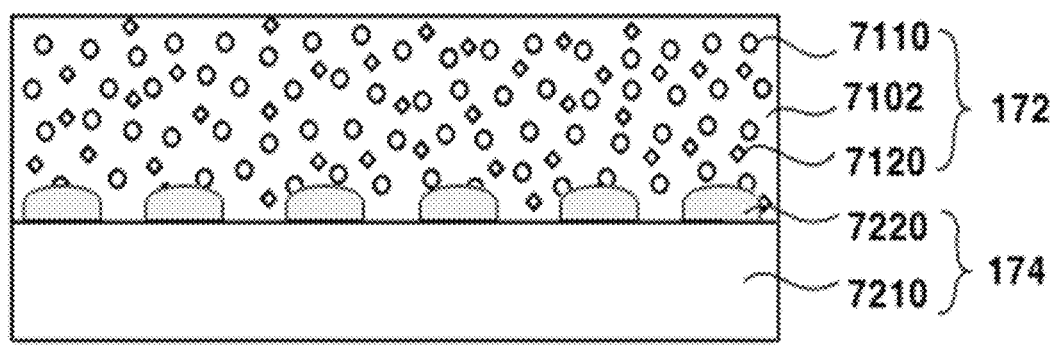
FIG. 6 is a cross-sectional view illustrating a fluorescence sensor assembly shown in FIG. 1.

FIG. 6 is a cross-sectional view illustrating a fluorescence sensor assembly 170 shown in FIG. 1.

Referring to FIG. 6, the fluorescence sensor assembly 170 includes an emission filter 172 and a single sensor 174 that constitutes a fluorescence sensor array or array.

The emission filter 172 is integrally formed on a single sensor 174 constituting a fluorescence sensor array or an array. The emission filter 172 shields an excitation light generated in a light source (not shown) and transmit an emission light emitted in a reaction space 240.

The emission filter 172 includes a base medium 7102, a semi-cured photoresist 7110 and a pigment 7120.

The base medium 7102 is disposed in a flat shape on a single sensor 174 constituting a fluorescent sensor array or an array to constitute an appearance of the emission filter 172. The base medium 7102 may be made of a transparent synthetic resin, glass, metal oxide, or the like. In the present embodiment, the base medium 7102 may include an epoxy resin, a silicone resin, or the like that does not generate fluorescence or phosphorescence and has biocompatible characteristics.

The semi-cured photoresist 7110 is dispersed in a base medium 7102 to include a photoresist fixed in a solid state by thermal curing, drying, photo-curing or the like. For one example, the semi-cured photoresist 7110 may include a negative photoresist. In another example, the semi-cured photoresist 7110 may include a positive photoresist.

Although it is not intended to limit the scope of the present invention by the theory, the reason why the emission filter 172 of the present invention has unique excellent optical characteristics to explain the present invention in more detail will be described below.

A typical color filter includes a pigment immobilized within a transparent medium and selectively transmits light in a manner that absorbs light of a certain wavelength into the pigment and transmits light of other wavelengths. The photoresist is characterized in that its chemical and optical characteristics are changed in response to short wavelength light such as ultraviolet light, blue light and green light. Accordingly, when the semi-cured photoresist 7110 is used for a color filter, there is a problem that the optical characteristics are changed over time. Therefore, the conventional color filter can be made of a thermosetting material that is completely saturated with light having a short wavelength such as ultraviolet light, blue light, green light, or the like, even if light having a short wavelength is irradiated thereto.

However, since the emitter filter 172 of the present invention is used in a disposable laboratory equipment not used for a long time, it is not necessary to maintain the same optical characteristic for a long time and only the optical characteristic is temporarily maintained for a relatively short experiment time. Specifically, when light having a short wavelength such as ultraviolet light, blue light, or green light is irradiated, the semi-cured photoresist 7110 absorbs light having a short wavelength for a predetermined period of time. The semi-cured photoresist 7110 temporarily functions as an optical filter with excellent characteristics, and over time, it is saturated with light having a short wavelength, thereby largely losing optical filter function. Therefore, in a conventional color filter, the semi-cured photoresist 7110 contrary to long-term stability could not be used.

In the present invention, on the contrary, in the process of stabilizing the semi-cured photoresist 7110 by being saturated with light having a short wavelength such as ultraviolet rays, blue light, or green light, by using the property of absorbing light having a short wavelength, an emission filter 172 having very excellent optical characteristics usable in the experimental apparatus is implemented. That is, in the present invention, by primarily blocking the excitation light by the pigment 7120 and secondarily blocking the excitation light by the semi-cured photoresist 7110, an emitter filter 172 having excellent characteristics regardless of the direction of the incident light which could not be obtained by a conventional color filter or an interference filter was manufactured.

The pigment 7120 may have a material that absorbs light of a certain wavelength. For example, a yellow pigment, a red pigment, a blue pigment, a green pigment, or the like may be used as the pigment 7120. In the present exemplary embodiment, the pigment 7120 includes a yellow pigment. Examples of the yellow pigment may include inorganic dyes such as lead chromate, calcium yellow, yellow oxides, complex inorganic color pigments, bismuth vanadate, and the like. Alternatively, examples of the yellow pigment may include organic dyes such as arylamide, diarylide, benzimidazolone, disazo ondensation, organic metal complexes, isoindoline, quinophthalone, anthrapyrimidine, flavanthrone, and the like.

A single sensor 174 that constitutes a fluorescence sensor array or an array includes a base substrate 7210 and a plurality of fluorescence sensors 7220.

The base substrate 7210 has a flat plate shape. The base substrate 7210 is integrally formed with the emission filter 172.

Fluorescent sensors 7220 may be implemented in CMOS. The fluorescence sensors 7220 are arranged in an array, and disposed on an upper portion of the base substrate 7210 to sense fluorescence. The detection of the fluorescence may be performed by a time-division method or a wavelength-division method.

In the case of the above-described time-division method, as the fluorescent material emits an emission light in response to an excitation light, a single sensor constituting a fluorescent sensor array or an array detects the emission light passing through the emission filter and senses the fluorescence by obtaining a time constant of the detected emission light.

In the case of the above-described wavelength-division method, as the fluorescent material emits an emission light in response to an excitation light, a single sensor constituting a fluorescent sensor array or an array detects the emission light passing through the emission filter and senses the fluorescence through spectral analysis of the detected emission light.

According to the present embodiment, it may directly measure the chemiluminescence signal on a surface of the fluorescence sensor assembly 170, thereby minimizing the loss of the optical signal and improving the measurement sensitivity.

In addition, when a position-based substance that binds to multiple antibodies or multiple antigens is attached to the fluorescence sensor assembly 170 rather than the reaction chamber 160 in a dot form, which is an array of rows and columns, the exact location of the dots may be identified on a pixel-by-pixel basis so that a location-based multi-sample and multiplex-based screening is possible.

In the present embodiment, the fluorescence sensor assembly 170 has a flat shape. The bottom surface of the reaction chamber 160 is flatly disposed on the flat fluorescent sensor assembly 170. Accordingly, even if blood is repeatedly moved in a first direction after the blood moves in a second direction in the reaction chamber 160 and then moved in the first direction, there is no obstacle in the movement of the blood. Even if the position-based material is attached on the fluorescent sensor assembly 170 in a dot form, the size of the position-based material is minute so that the movement of liquid such as blood does not interfere.

Referring again to FIG. 1, an outlet 182 for discharging a sample such as blood or a cleaning liquid, which the reaction is terminated, is formed in the output chamber 180. That is, a plurality of receptors that react with a sample such as blood in the reaction chamber 160 and detect the biochemical material contained in the sample are detected for the biochemical material contained in the sample. After the reaction, the sample and the receptors may be discharged from the reaction chamber 160 through the outlet 182 to the outside. Additionally, a waist pad (or absorbent pad) (not shown) that absorbs the reacted sample and a plurality of receptors may be disposed on an upper portion of the outlet 182.

The air button 190 is connected to the output chamber 180 to supply air to the output-micro flow path via the output chamber 180. Thus, the flow of the sample located in the output-micro flow path is changed not in the forward direction flowing out of the reaction chamber 160 but in the reverse direction toward the reaction chamber 160. Thus, the probability that the sample reacts in the reaction chamber 160 may be further increased.

As described above, according to the present invention, since the bottom surface of the reaction chamber and the upper surface of the fluorescence sensor assembly are arranged to coincide with each other, even if fluid is repeatedly moved in a first direction after the fluid moves in a second direction in the reaction chamber and then moved in the first direction, there is no obstacle in the movement of the fluid.

Thus, it is possible to increase the probability of antigen-antibody reaction in the reaction chamber. Further, blood is supplied to the reaction chamber by pressurization of the inlet, and the direction of movement of the blood in the reaction chamber is changed by pressing the air button, thereby speeding up the blood movement speed. Thus, it is possible to increase the likelihood of exposure to an antigen-antibody reaction between an antibody or antigen mixed with a location-based material (e.g., a hydrogel pad) and an antigen or antibody contained in the blood.

Moreover, the fluid in the blister (e.g., a cleaning liquid) is supplied to the reaction chamber through a method of pressurizing various blisters, and the direction of movement of the fluid in the reaction chamber is changed through a method of pressing the air button, thereby increasing the moving speed of the fluid. Therefore, the cleaning probability of contaminated portions other than the hydrogel pad may be increased. Thus, the reliability of the antigen-antibody reaction may be improved while increasing the speed of the antigen-antibody reaction, and the sensitivity of the reaction may be improved by closely matching the positions of reactants between the sensor and the antigen-antibody.

The foregoing is illustrative of the present invention and is not to be construed as limiting thereof. Although a few exemplary embodiments of the present invention have been described, those skilled in the art will readily appreciate that many modifications are possible in the exemplary embodiments without materially departing from the novel teachings and advantages of the present invention. Accordingly, all such modifications are intended to be included within the scope of the present invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific exemplary embodiments disclosed, and that modifications to the disclosed exemplary embodiments, as well as other exemplary embodiments, are intended to be included within the scope of the appended claims. The present invention is defined by the following claims, with equivalents of the claims to be included therein.

What is claimed is:

1. An immunoassay cartridge comprising:
   a reaction chamber comprising an inner surface including a bottom surface;
   a plurality of antibodies or antigens;
   a location-based material comprising dendron that is mixed with the plurality of antibodies or antigens, the location-based material being attached to the inner surface of the reaction chamber in the form of dots arranged rows and columns; and
   a fluorescence sensor assembly disposed on the bottom surface of the reaction chamber, wherein
   the fluorescence sensor assembly photographs an image in plan view for image analysis in which a luminescent signal generated by an immune reaction in each dot is measured for each pixel and the microscopic signal is interpreted as a meaningful value,
   the bottom surface of the reaction chamber includes an upper surface of the fluorescence sensor assembly, and
   the bottom surface of the reaction chamber and the upper surface of the fluorescence sensor assembly are coplanar.

2. The immunoassay cartridge of claim 1, further comprising:
   an input-micro flow path formed between an inlet and the reaction chamber;
   one or more blisters; and
   a sub-micro flow path formed between the blister and the input-micro flow path.

3. The immunoassay cartridge of claim 2, further comprising:
   a valve disposed in the sub-micro flow path to control a flow of a fluid.

4. The immunoassay cartridge of claim 2, further comprising:
   an output-micro flow path connected to the reaction chamber;
   an output chamber connected to the reaction chamber through the output-micro flow path; and
   an air button connected to the output chamber, the air button supplying air to the output-micro flow path via the output chamber in response to an operation of an operator thereby allowing for reversing flow direction in the output-micro low path toward the reaction chamber.

5. The immunoassay cartridge of claim 1, wherein the fluorescence sensor assembly comprises:
   an emission filter disposed below the reaction chamber, the emission filter having an optical characteristic capable of filtering regardless of an incident angle of the excitation light and transmitting a radiation light having a wavelength larger than that of the excitation light.

6. The immunoassay cartridge of claim 5, wherein the fluorescence sensor assembly further comprises:
   a single sensor disposed below the emission filter, the single sensor constituting a fluorescent sensor array or an array measuring the luminance of the emission light that has passed through the emission filter.

7. The immunoassay cartridge of claim 5, wherein the emission filter comprises:
   a base medium arranged in a flat shape and including a material which is transparent and which does not generate fluorescence or phosphorescence by excitation light;
   a photoresist disposed in the base medium and fixed in a solid state by at least one method selected from the group consisting of thermosetting, photocuring and drying; and
   a pigment disposed in the base medium and absorbing light of a predetermined wavelength.

8. The immunoassay cartridge of claim 6, wherein the single sensor comprises:
   a base substrate having a flat plate shape and integrally formed with the emission filter; and
   a plurality of fluorescence sensors embedded in an upper portion of the base substrate, the fluorescence sensors arranged in an array so that the upper surface of the base substrate is planar.

9. The immunoassay cartridge of claim 1, further comprising a printed circuit board electrically connected to the fluorescent sensor assembly through solder balls.

10. The immunoassay cartridge of claim 1, wherein the fluorescence sensor assembly has a flat shape, and a bottom surface of the reaction chamber and an upper surface of the fluorescence sensor assembly are aligned with each other.

11. The immunoassay cartridge of claim 1, wherein the location-based material further comprises hydrogel pad.

12. An immunoassay cartridge comprising:
    a reaction chamber comprising an inner surface including a bottom surface;
    a plurality of antibodies or antigens attached to the inner surface of the reaction chamber; and
    a fluorescence sensor assembly disposed on the bottom surface of the reaction chamber, wherein
    the fluorescence sensor assembly photographs an image in plan view for image analysis in which a luminescent signal generated by an immune reaction in each dot is measured for each pixel and the microscopic signal is interpreted as a meaningful value,
    the bottom surface of the reaction chamber includes an upper surface of the fluorescence sensor assembly,
    the bottom surface of the reaction chamber and the upper surface of the fluorescence sensor assembly are coplanar,
    the fluorescence sensor assembly comprises:
      an emission filter disposed below the reaction chamber, the emission filter having an optical characteristic capable of filtering regardless of an incident angle of the excitation light and transmitting a radiation tight having a wavelength larger than that of the excitation light; and a single sensor disposed below the emission filter, the single sensor constituting a fluorescent sensor array or an array measuring the luminance of the emission light that has passed through the emission filter, and the emission filter comprises:
  a base medium arranged in a flat shape and including a material which is transparent and which does not generate fluorescence or phosphorescence by excitation light;
  a photoresist disposed in the base medium and fixed in a solid state by at least one method selected from the group consisting of thermosetting, photocuring and drying; and
  a pigment disposed in the base medium and absorbing light of a predetermined wavelength.

* * * * *